(12) United States Patent  
Aaron

(10) Patent No.: US 9,039,776 B2  
(45) Date of Patent: May 26, 2015

(54) INTERVERTEBRAL-DISC PROSTHESIS

(75) Inventor: Alain Aaron, Saint Witz (FR)

(73) Assignee: FOURNITURES HOSPITALIERES INDUSTRIE (FR)

( * ) Notice: Subject to any disclaimer, the term of this patent is extended or adjusted under 35 U.S.C. 154(b) by 27 days.

(21) Appl. No.: 14/000,791

(22) PCT Filed: Feb. 10, 2012

(86) PCT No.: PCT/FR2012/050296  
§ 371 (c)(1),  
(2), (4) Date: Nov. 4, 2013

(87) PCT Pub. No.: WO2012/114017  
PCT Pub. Date: Aug. 30, 2012

(65) Prior Publication Data  
US 2014/0100661 A1    Apr. 10, 2014

(30) Foreign Application Priority Data  
Feb. 21, 2011    (FR) ...................................... 11 51393

(51) Int. Cl.  
*A61F 2/44* (2006.01)  
*A61F 2/46* (2006.01)  
*A61F 2/30* (2006.01)

(52) U.S. Cl.  
CPC .............. *A61F 2/442* (2013.01); *A61F 2/4611* (2013.01); *A61F 2002/30187* (2013.01);  
(Continued)

(58) Field of Classification Search  
CPC ..... A61F 2/442; A61F 2/4455; A61F 2/4611; A61F 2/447  
USPC ..................................................... 623/17.16  
See application file for complete search history.

(56) References Cited

U.S. PATENT DOCUMENTS

2005/0060035 A1    3/2005 Errico et al.  
2006/0276900 A1*  12/2006 Carpenter .................. 623/17.15  
(Continued)

FOREIGN PATENT DOCUMENTS

WO    2006055168 A2    5/2006  
WO    2010094881 A1    8/2010

OTHER PUBLICATIONS

International Search Report issued May 29, 2012 re: PCT/FR2012/050296; citing: WO 2010/094881 A1, US 2007/073311 A1, US 2005/060035 A1 and WO 2006/055168 A2.  
Written Opinion issued May 29, 2012 re: PCT/FR2012/050296; citing: WO 2010/094881.

*Primary Examiner* — Jerry Cumberledge  
*Assistant Examiner* — Tessa Matthews  
(74) *Attorney, Agent, or Firm* — Cantor Colburn LLP

(57) ABSTRACT

The intervertebral disc prosthesis comprises first and second plates (3, 4) designed to be attached on one of the two vertebrae adjacent to the intervertebral disc to be replaced, and a compression pad arranged between the first and second plates. Each plate comprises first attaching means including two attaching portions (14a, 14b) positioned symmetrically on either side of the anteroposterior median plane of said plate, second attaching means including two attaching portions (15a, 15b) positioned symmetrically on either side of a first plane inclined by an angle comprised between 50° and 70° relative to the anteroposterior median plane of said plate, and third attaching means opposite the second attaching means relative to the anteroposterior median plane and including two attaching portions (16a, 16b) positioned symmetrically on either side of a second plane inclined by an angle of approximately 90°, relative to the anteroposterior median plane of said plate.

8 Claims, 4 Drawing Sheets

(52) U.S. Cl.
CPC ........... *A61F 2002/30354* (2013.01); *A61F 2002/30563* (2013.01); *A61F 2002/30822* (2013.01); *A61F 2002/30823* (2013.01); *A61F 2002/30827* (2013.01); *A61F 2002/30841* (2013.01); *A61F 2310/00023* (2013.01); *A61F 2/30742* (2013.01); *A61F 2002/30332* (2013.01); *A61F 2002/30372* (2013.01)

(56) References Cited

U.S. PATENT DOCUMENTS

| | | | |
|---|---|---|---|
| 2007/0073311 A1 | 3/2007 | Williams et al. | |
| 2008/0161922 A1* | 7/2008 | Rhoda | 623/17.11 |
| 2010/0286784 A1* | 11/2010 | Curran et al. | 623/17.16 |
| 2012/0116513 A1* | 5/2012 | Carpenter | 623/17.16 |
| 2012/0158143 A1* | 6/2012 | Shapiro | 623/17.16 |

* cited by examiner

INTERVERTEBRAL-DISC PROSTHESIS

TECHNICAL FIELD

The present invention relates to a prosthesis designed to replace a damaged intervertebral disc of the spinal column.

BACKGROUND

The spinal column is made up of a set of superimposed vertebrae connected to each other by fibrocartilaginous discs, called intervertebral discs. These intervertebral discs play a fundamental role in the statics and dynamics of the spinal column: they ensure the mobility of the vertebrae with respect to one another.

These intervertebral discs are often subject to disorders relative to compression of vertebrae, herniated discs, vertebral movement, or intervertebral arthrosic degeneration. These disorders are most often a source of pain or functional bother not responding to medical treatment; in some cases, they may even be incapacitating.

The methods used to soothe patients suffering from these disorders may consist of a surgical operation seeking to replace the damaged disc with an intervertebral disc prosthesis.

The implantation of such an intervertebral disc prosthesis may be done using different approaches in particular depending on the anatomy of the patient. There are three main approaches for the L1/L2 to L5/S1 lumbar stages, namely:
- the retroperitoneal anterior approach, generally possible for all lumbar stages, but which may sometimes present difficulties due to the presence of veins and arteries,
- the lateral approach, possible for all lumbar stages except L5/S1, which is statistically one of the stages most often needing the implantation of a prosthesis, due to the bother caused by the presence of the iliac wings,
- the anterolateral approach, which is possible for all lumbar stages, but requires a more difficult oblique prosthesis placement path.

Document WO 2010/094881 describes an intervertebral disc prosthesis comprising first and second plates, each fixed on one of the two vertebrae adjacent to the vertebral disc to be replaced, between which a compression pad is positioned. Each plate includes, on the inner face thereof, two cavities emerging in the anterior face of the corresponding plate and positioned on either side of the anteroposterior plane of said plate, the cavities of the first plate being arranged to be situated across from the cavities of the second plate so as to form two hollows making it possible to attach a gripper-impactor and implant the prosthesis using the anterior approach.

The prosthesis described in document WO 2010/094881 does not allow implantation using the lateral approach, and only allows implantation using the anterolateral approach for very experienced surgeons. As a result, when veins and arteries make it complicated to perform the implantation using the anterior approach, a surgeon having a prosthesis similar to that described in document WO 2010/094881 is often forced, in place of that intervertebral disc prosthesis, to implant an intervertebral arthrodesis using the anterior approach. The implantation of such an arthrodesis involves fusing two vertebrae adjacent to the damaged disc. The main drawback of this method is that it eliminates all mobility between the two vertebrae adjacent to the damaged disc, and therefore concentrates the mechanical stresses on the adjacent intervertebral discs, which can cause a risk of deterioration of their articular surface.

In order to avoid implanting such an arthrodesis when the anterior approach is not possible, it is known to provide surgeons with an intervertebral disc prosthesis having attaching means arranged to cooperate with complementary attaching means of a gripper-impactor, the attaching means formed on the prosthesis being designed so as to allow gripping of the prosthesis in a latero-lateral direction using a gripper-impactor, and therefore to implant the prosthesis using the lateral approach.

Thus, in order to allow a surgeon to implant an intervertebral disc prosthesis on a patient using different approaches, it is necessary to provide the latter with at least two lines of prostheses, namely a first line of prostheses of different sizes adapted for implantation using the anterior approach and a second line of prostheses of different sizes adapted for implantation using the lateral approach, as well as a plurality of ancillaries adapted for placing said prostheses.

This high number of prostheses and ancillaries complicates the storage thereof and increases the costs related thereto. Furthermore, this high number of disc prostheses complicates the handling of the latter by the operating personnel, and makes the operating gesture more complicated.

This results in a large number of prostheses and ancillaries to be provided to the surgeon, which makes the operating gesture more complex.

It should be noted that the approach selection planned by the surgeon before the operation may be modified during the operation, due to the presence of tissues making the placement of the prosthesis using the approach initially selected complex.

In this scenario, a new prosthesis must be selected from the line of prostheses suitable for implantation using the approach selected by the surgeon during the operation, and the initially selected prosthesis must be discarded, which also increases the operating time and the costs of the surgical operation.

Furthermore, the selection of a new prosthesis requires the use of a new ancillary, which increases the number of ancillaries to be sterilized after the surgical operation.

BRIEF SUMMARY

The present invention aims to resolve these drawbacks.

The technical problem at the base of the invention therefore concerns providing an intervertebral disc prosthesis that is simple to produce, has a compact structure, and is completely safe to use, while making it possible to simplify the surgical operation.

To that end, the present invention relates to an intervertebral disc prosthesis, which comprises first and second rigid plates each comprising an inner face and an outer face designed to be attached on one of the two vertebrae adjacent to the intervertebral disc to be replaced, and a compression pad arranged between the first and second plates and secured to the inner faces of the first and second plates, characterized in that each plate comprises first attaching means including two attaching portions positioned substantially symmetrically on either side of the anteroposterior median plane of said plate, second attaching means including two attaching portions positioned substantially symmetrically on either side of a first plane substantially perpendicular to the inner face of said plate and inclined by an angle comprised between 50° and 70° relative to the anteroposterior median plane of said plate, and third attaching means opposite the second attaching means relative to the anteroposterior median plane and including two attaching portions positioned substantially symmetrically on either side of the same plane substantially perpendicular to the inner face of said plate and inclined by an angle comprised between 85° and 95°, preferably approximately 90°, relative to the anteroposterior median plane of said plate, in that the first, second and third attaching means formed on the first plate are arranged to be situated respectively across from the first, second and third attaching means formed on the second plate, and in that the first, second and third attaching means of the first and second plates are designed to cooperate respectively with complementary attaching means mounted on a gripping member.

The configuration of the different attaching means of the prosthesis according to the invention allows easy implantation of the latter using the three aforementioned approaches, namely the anterior approach by having the first attaching means of the two plates cooperate with the complementary attaching means of a gripping member; the anterolateral approach by having the second attaching means of the two plates cooperate with the complementary attaching means of a gripping member; and the lateral approach by having the third attaching means of the two plates cooperate with the complementary attaching means of a gripping member.

These arrangements give surgeons the possibility of implanting an intervertebral disc prosthesis using the three aforementioned approaches, by providing them with a single line of prostheses. This results in a significant decrease in the number of prostheses to be provided to surgeons, and therefore a simplification of the operating gesture.

These arrangements also allow the surgeon to modify his choice of approach during the operation, while keeping the same prosthesis, which further simplifies the operating gesture and limits the costs of the surgical operation.

These arrangements also make it possible to remove a prosthesis using the same approach as that used for the placement or using one of the other two possible approaches.

Preferably, the first, second and third attaching means of the first and second plates have a substantially identical geometry and dimensions. These arrangements make it possible to implant a prosthesis with the same ancillary irrespective of the selected approach.

Preferably, each plate includes a convex anterior face at least partially delimited by a cylindrical surface portion extending over an angle greater than 160° and having a constant curve radius. The cylindrical surface portion preferably extends over an angle comprised between 160° and 220°, and for example over an angle of approximately 180°.

Advantageously, the axis of the cylindrical surface portion of each plate extends substantially perpendicular to the inner face of said plate and extends substantially in the anteroposterior median plane of said plate.

Preferably, each plate has a maximum width at the anteroposterior median plane of said plate. It should be noted that the width of a plate refers to the dimension of that plate in an anteroposterior direction, and the length of a plate refers to the dimension of that plate in a latero-lateral direction.

Advantageously, for each plate, the intersection between the first plane and the anteroposterior median plane of said plate is substantially combined with the axis of the cylindrical surface portion of said plate.

According to one embodiment of the invention, for each plate, the intersection between the second plane and the anteroposterior median plane of said plate is substantially combined with the axis of the cylindrical surface portion of said plate.

According to another embodiment of the invention, for each plate, the intersection between the second plane and the anteroposterior median plane of said plate is offset relative to the intersection between the first plane and the anteroposterior median plane of said plate. According to this embodiment, for each plate, the intersection between the second plane and the anteroposterior median plane of said plate may for example be distant from the intersection between the first plane and the anteroposterior median plane of said plate by a distance substantially corresponding to half of the maximum width of said plate. According to this embodiment, for each plate, the intersection between the second plane and the anteroposterior median plane of said plate may for example be distant from the anterior face of said plate by a distance substantially corresponding to half of the maximum width of said plate. According to this embodiment, the intersection between the second plane and the anteroposterior median plane of said plate is advantageously offset with respect to the axis of the cylindrical surface portion of said plate.

According to one advantageous feature of the invention, the curve radius of the cylindrical surface portion of each plate is substantially equal to half of the maximum length of said plate.

Preferably, the ratio between the maximum width and the maximum length of each plate is comprised between 0.66 and 0.75.

According to one embodiment of the invention, each attaching portion is formed at least partially by an attaching rim delimited by a notch formed in the corresponding plate and emerging in the periphery of said plate.

Preferably, each notch extends over a portion of the thickness of the corresponding plate and emerges in the inner face of said plate. These arrangements make it possible to preserve an optimized bearing surface of the prosthesis on the vertebral bone bodies, and to form an area that ensures positioning in a plane of the gripper-impactor.

Advantageously, the outer face of the first plate and the outer face of the second plate form an angle comprised between 10° and 20°.

Preferably, the first plate includes, in the central area thereof, a tubular part turned toward the second plate, and the second plate includes, in its central area, a stud with a section smaller than that of the tubular part, turned toward the first plate and engaged in the tubular part.

BRIEF DESCRIPTION OF THE DRAWINGS

In any case, the invention will be well understood using the following description in light of the appended diagrammatic drawing showing, as non-limiting examples, three embodiments of this intervertebral disc prosthesis.

DETAILED DESCRIPTION

Figure 1:
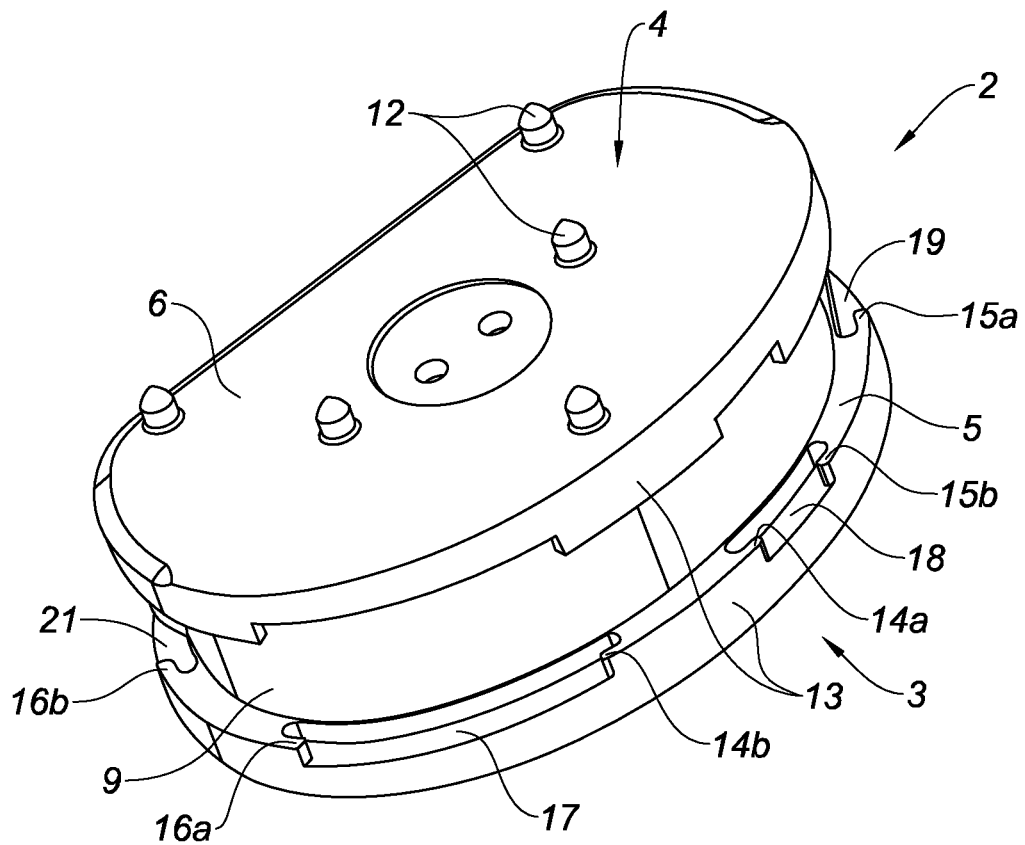
FIG. 1 is a perspective view of an intervertebral disc prosthesis according to a first embodiment of the invention.

FIGS. 1 to 5 show a lumbar intervertebral disc prosthesis 2 designed to replace a damaged lumbar intervertebral disc.

The prosthesis 2 includes a lower plate 3 and an upper plate 4. The two plates 3, 4 are preferably made from titanium-based alloys.

Each plate 3, 4 comprises an inner face 5 and an outer face 6 that are substantially planar. The outer face 6 of each plate 3, 4 is designed to be fixed on one of the two lumbar vertebrae adjacent to the intervertebral disc to be replaced. As shown more particularly in FIG. 3, the outer face 6 of the lower plate and the outer face 6 of the upper plate preferably form an angle comprised between 10° and 20°.

Figure 2:
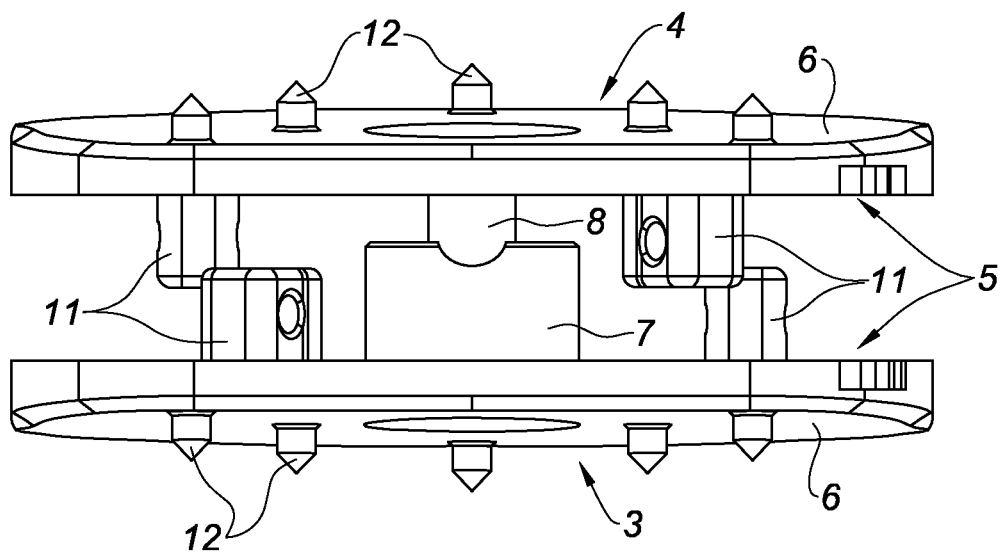
FIG. 2 is a rear view of two plates of the prosthesis of FIG. 1.
Figure 3:
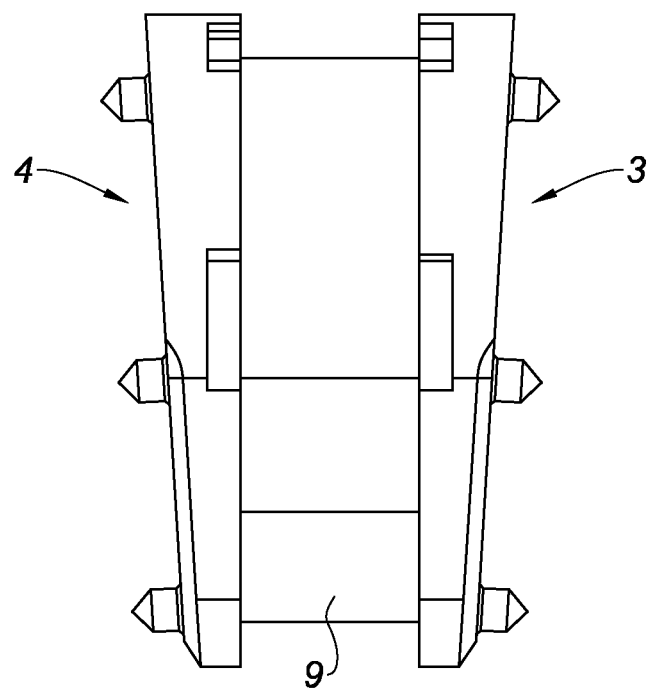
FIG. 3 is a side view of the prosthesis of FIG. 1.

As shown in FIG. 2, the lower plate 3 includes, in the central area thereof, a tubular part 7 with a circular section turned toward the upper plate 4. The upper plate 4 includes, in its central area, a cylindrical or frustoconical stud 8 with a section smaller than that of the tubular part 7, turned toward the lower plate 3 and engaged in the tubular part 7. It must be noted that the sum of the lengths of the tubular part 7 and the stud 8 is greater than the distance between the two plates 3, 4.

The prosthesis 2 further includes a compression pad 9 positioned between the lower and upper plates 3, 4, including in the volume comprised between the tubular part 7 and the stud 8. The compression pad 9 is secured to the lower faces 5 of the two plates. The compression pad 9 is advantageously made from a compressible material, preferably of the polycarbonate urethane type.

As shown in FIG. 2, each plate 3, 4 includes, on its inner face 5, i.e., on its face turned toward the other plate, lugs 11 favoring attaching of the compression pad 9. Furthermore, each plate 3, 4 includes, on its outer face 6, fasting tips 12 designed to favor the fastening on the vertebra against which it is designed to be in contact.

Each plate 3, 4 includes a convex anterior face 13 delimited by a cylindrical surface portion extending over an angle comprised between 180° and 220°, and having a constant curve radius R. The axis A of the cylindrical surface portion of each plate extends substantially perpendicular to the inner face 5 of the plate and extends substantially in the anteroposterior median plane $P_1$ of said plate. The curve radius R of the cylindrical surface portion of each plate is substantially equal to half of the maximum length $L_1$ of said plate.

The ratio between the maximum width $L_2$ and the maximum length $L_1$ of each plate is preferably comprised between 0.66 and 0.75.

Each plate further includes first, second and third attaching means arranged to cooperate with complementary attaching means mounted on a gripping member, respectively. The first, second and third attaching means formed on the lower plate are arranged to be situated across from first, second and third attaching means formed on the upper plate, respectively.

The first attaching means of each plate include two attaching portions 14a, 14b positioned substantially symmetrically on either side of the anteroposterior median plane $P_1$ of said plate.

The second attaching means of each plate include two attaching portions 15a, 15b positioned substantially symmetrically on either side of a first plane $P_2$ substantially perpendicular to the inner face 5 of said plate and inclined by an angle α comprised between 50° and 70° relative to the anteroposterior median plane $P_1$ of said plate. The angle α is for example equal to approximately 55° or approximately 60°.

The third attaching means of each plate are opposite the second attaching means relative to the anteroposterior median plane $P_1$ and include two attaching portions 16a, 16b positioned substantially symmetrically on either side of a second plane $P_3$ substantially perpendicular to the inner face 5 of said plate and inclined by an angle β comprised between 85° and 95°, and preferably approximately 90°, relative to the anteroposterior median plane $P_1$ of said plate.

For each plate, the intersection between the first plane $P_2$ and the anteroposterior median plane $P_1$ of said plate and the intersection between the second plane $P_3$ and the anteroposterior median plane $P_1$ of said plate are substantially combined with the axis A of the cylindrical surface portion of said plate.

Each plate further comprises a plurality of notches angularly offset with respect to one another and emerging in the periphery of said plate.

Figure 4:
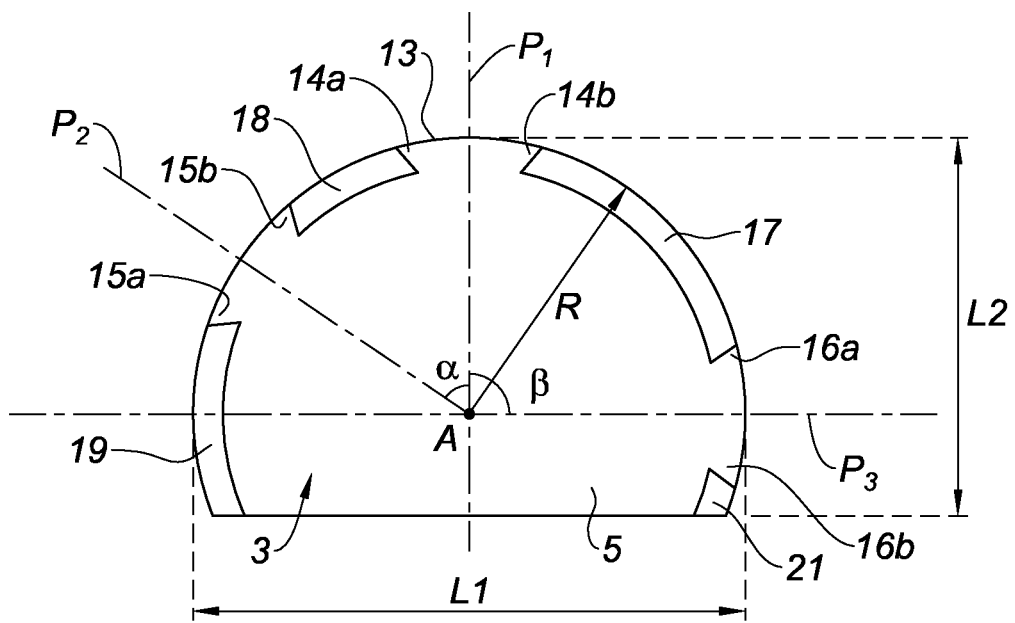
FIG. 4 is a diagrammatic top view of one of the plates of the prosthesis of FIG. 1.
Figure 5:
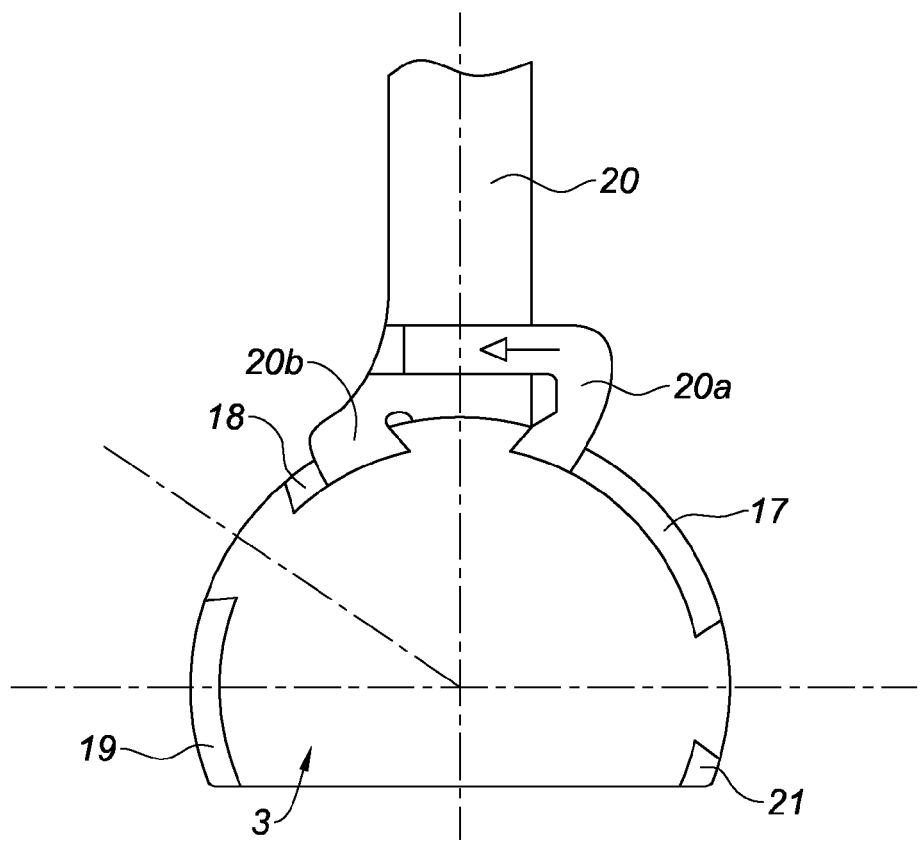
FIG. 5 is a top view of the plate of FIG. 4, on which a gripping member of a first type is mounted.

As shown in FIGS. 1, 4 and 5, each plate 3, 4 more particularly comprises a first notch 17 delimiting two attaching rims respectively forming the attaching portions 14b, 16a, a second notch 18 delimiting two attaching rims respectively forming the attaching portions 14a, 15b, a third notch 19 delimiting an attaching rim forming the attaching portion 15a, and lastly a fourth notch 21 delimiting an attaching rim forming the attaching portion 16b.

Each notch advantageously extends over a portion of the thickness of the corresponding plate and emerges in the inner face 5 of said plate. Each notch is preferably configured such that the or each corresponding attaching rim is inwardly delimited by a concave inner wall, for example in the form of a half-dovetail (see FIGS. 4 and 5) or a partial cylinder shape (see FIG. 1).

It should be noted that the different attaching means of the prosthesis shown in FIGS. 1 to 5 are arranged to cooperate with a gripping member 20 that holds the prosthesis by gripping its attaching portions 20a, 20b, as more particularly shown in FIG. 5.

It should also be noted that irrespective of the selected approach, therefore irrespective of the selected attaching means, the impaction forces exerted on the prosthesis by the gripping member are exclusively transmitted to the plates, without stressing the compression pad 9.

According to one embodiment not shown in the figures, each plate may include six notches angularly offset with respect to one another, each notch delimiting a single attaching rim.

Figure 6:
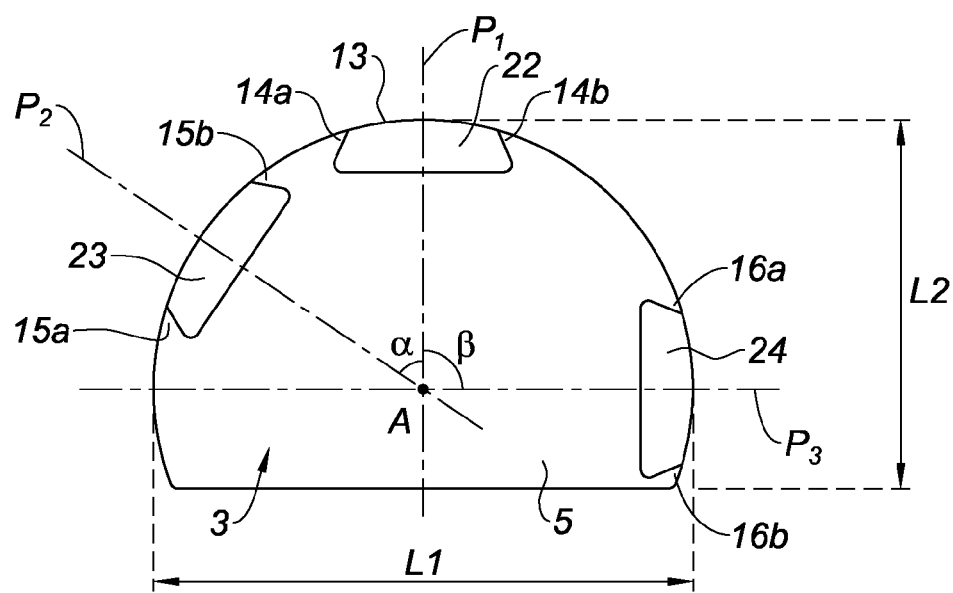
FIG. 6 is a diagrammatic top view of one of the plates of an intervertebral disc prosthesis according to a second embodiment of the invention.

According to a second embodiment shown in FIG. 6, each plate comprises only three notches angularly offset with respect to one another. The first notch 22 delimits the attaching rims forming the attaching portions 14a, 14b belonging to the first attaching means, the second notch 23 delimits the attaching rims forming the attaching portions 15a, 15b belonging to the second attaching means, and the third notch 24 delimits the attaching rims forming the attaching portions 16a, 16b belonging to the third attaching means.

Figure 7:
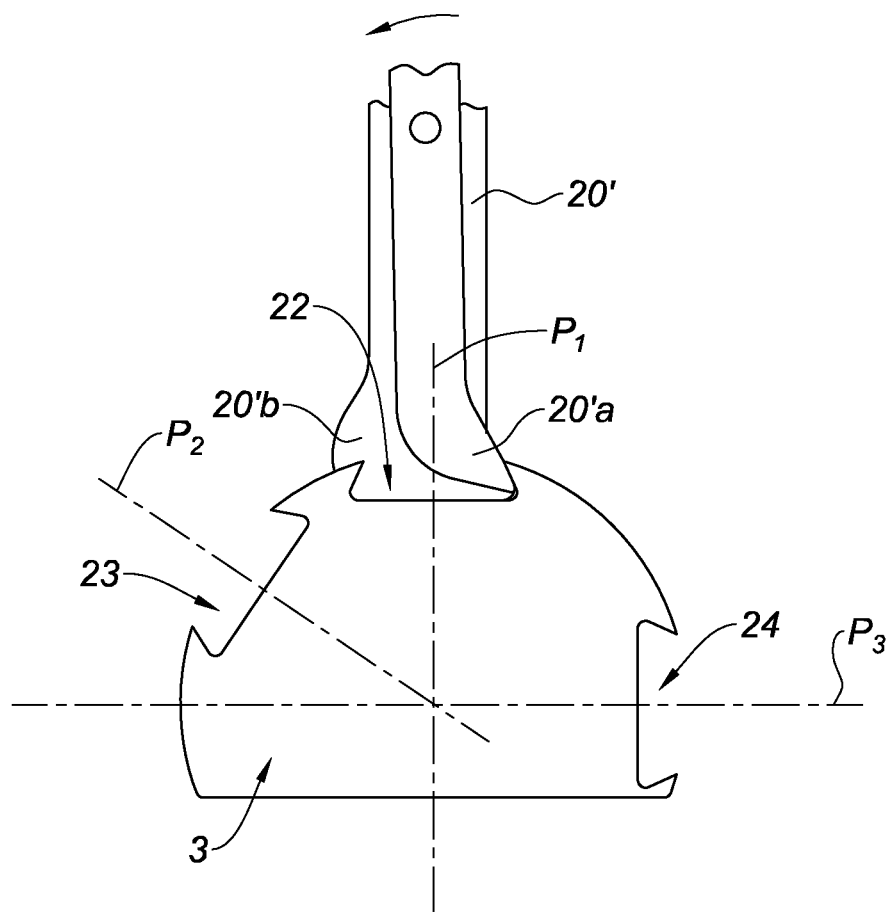
FIG. 7 is a diagrammatic top view of one of the plates of an intervertebral disc prosthesis according to a third embodiment of the invention, on which a gripping member of a second type is mounted.

It should be noted that the different attaching means of the prosthesis shown in FIG. 6 are arranged to cooperate with a gripping member 20' which holds the prosthesis by separating its attaching portions 20'a, 20'b, as more particularly shown in FIG. 7.

According to the embodiment shown in FIG. 7, each notch is a through notch and respectively emerges in the inner and outer faces of said plate.

According to one embodiment not shown in the figures, for each plate, the intersection between the second plane and the anteroposterior median plane of said plate is offset with respect to the intersection between the first plane and the anteroposterior median plane of said plate. For example, the intersection between the second plane $P_3$ and the anteroposterior median plane $P_1$ of said plate is distant from the anterior face 5 of said plate by a distance substantially corresponding to half of the maximum width $L_2$ of said plate.

The invention is of course not limited solely to the embodiments of this intervertebral disc prosthesis described above as examples, but on the contrary encompasses all alternative embodiments.

The invention claimed is:

1. An intervertebral disc prosthesis, comprising:

first and second rigid plates each comprising an inner face and an outer face designed to be attached on one of two vertebrae adjacent to an intervertebral disc to be replaced, each of the first and second plates comprises first attaching means including two first attaching portions positioned substantially symmetrically on either side of an anteroposterior median plane of said plate, second attaching means including two second attaching portions positioned substantially symmetrically on either side of a first plane substantially perpendicular to the inner face of said plate and inclined by a first angle comprised between 50° and 70° relative to the anteroposterior median plane of said plate, and third attaching means opposite the second attaching means relative to the anteroposterior median plane and including two third attaching portions positioned substantially symmetrically on either side of a second plane substantially perpendicular to the inner face of said plate and inclined by a second angle comprised between 85° and 95° relative to the anteroposterior median plane of said plate; and a compression pad arranged between the first and second plates and secured to the inner faces of the first and second plates;

wherein the first, second and third attaching means formed on the first plate are arranged to be situated respectively across from the first, second and third attaching means formed on the second plate, and the first, second and third attaching means of the first and second plates are designed to cooperate respectively with complementary attaching means mounted on a gripping member, wherein each of the first, second and third attaching portion is formed at least partially by an attaching rim delimited by a notch formed in the corresponding plate and emerging in a periphery of said plate, wherein each notch extends over a portion of a thickness of the corresponding plate and emerges in the inner face of said plate.

2. The intervertebral disc prosthesis according to claim 1, wherein each of the first and second plates includes a convex anterior face at least partially delimited by a cylindrical surface portion extending over an angle greater than 160° and having a constant curve radius.

3. The intervertebral disc prosthesis according to claim 2, wherein an axis of the cylindrical surface portion of each of the first and second plates extends substantially perpendicular to the inner face of said plate and extends substantially in the anteroposterior median plane of said plate.

4. The intervertebral disc prosthesis according to claim 3, wherein for each of the first and second plates, a first intersection between the first plane and the anteroposterior median plane of said plate is substantially combined with the axis of the cylindrical surface portion of said plate.

5. The intervertebral disc prosthesis according to claim 3, wherein for each of the first and second plates, a second intersection between the second plane and the anteroposterior median plane of said plate is substantially combined with the axis of the cylindrical surface portion of said plate.

6. The intervertebral disc prosthesis according to claim 2, wherein the curve radius of the cylindrical surface portion of each of the first and second plates is substantially equal to half of a maximum length of said plate.

7. The intervertebral disc prosthesis according to claim 1, wherein a ratio between a maximum width and the maximum length of each of the first and second plates is comprised between 0.66 and 0.75.

8. The intervertebral disc prosthesis according to claim 1, wherein the outer face of the first plate and the outer face of the second plate form an angle comprised between 10° and 20°.

* * * * *